United States Patent [19]

Davis, Jr.

[11] 4,276,779

[45] Jul. 7, 1981

[54] DYNAMICALLY FOCUSSED ARRAY

[75] Inventor: Luther Davis, Jr., Wayland, Mass.

[73] Assignee: Raytheon Company, Lexington, Mass.

[21] Appl. No.: 24,939

[22] Filed: Mar. 29, 1979

[51] Int. Cl.³ .......................................... G01N 29/00
[52] U.S. Cl. ..................................... 73/626; 367/105
[58] Field of Search ................. 73/625, 626, 628, 641, 73/642; 128/660; 367/103, 104, 105, 123, 125; 310/334, 335, 336

[56] References Cited

U.S. PATENT DOCUMENTS

| | | | |
|---|---|---|---|
| 3,402,598 | 9/1968 | Colgate | 73/629 |
| 3,504,368 | 3/1970 | Ruben | 343/701 |
| 3,530,475 | 9/1970 | Danielson | 343/754 |
| 3,587,561 | 6/1971 | Ziedonis | 128/660 |
| 3,618,696 | 11/1971 | Hurwitz | 367/150 |
| 3,709,029 | 1/1973 | Hurwitz | 73/625 |
| 3,859,984 | 1/1975 | Langley | 128/660 |
| 3,967,234 | 6/1976 | Jones . | |
| 4,011,750 | 3/1977 | Robinson | 73/628 |
| 4,012,952 | 3/1977 | Dory | 73/612 |
| 4,084,582 | 4/1978 | Nigam | 128/660 |
| 4,097,835 | 6/1978 | Green | 367/103 |
| 4,161,121 | 7/1979 | Zitelli et al. | 73/626 |
| 4,180,790 | 12/1979 | Thomas | 367/105 |
| 4,180,791 | 12/1979 | Tiemann | 73/626 |

OTHER PUBLICATIONS

M. Ueda et al., "Prototype of Dynamic Focusing Transducer," Bulletin of Tokyo Institute of Tech., No. 131, pp. 37–43, 1975.

*Primary Examiner*—Stephen A. Kreitman
*Attorney, Agent, or Firm*—Martin M. Santa; Joseph D. Pannone

[57] ABSTRACT

An array of sonic transducers, useful for medical ultrasonic imaging, has individual sections thereof separately coupled for forming separate beams of sonic energy which converge, respectively, to separate foci along a common axis of the beams. The ratio of the diameter of the radiating aperture of the array relative to a wavelength of the sonic energy is chosen to provide a moderate degree of focusing so that the depth of field at one focus blends with the depth of field of the next focus. Thereby, there is formed a continuous region of substantially uniform intensity of sonic radiation along the common beam axis. Circuitry is provided for selecting one or more specific foci dependent on the bounds of a selected region to be insonified. Upon reception of sonic energy, circuitry is provided for selecting one or more specific foci as a function of the time of travel of an echo from a subject being observed to approximate a continuously varying focus in accordance with distance from successive points of reflection within the subject.

7 Claims, 14 Drawing Figures

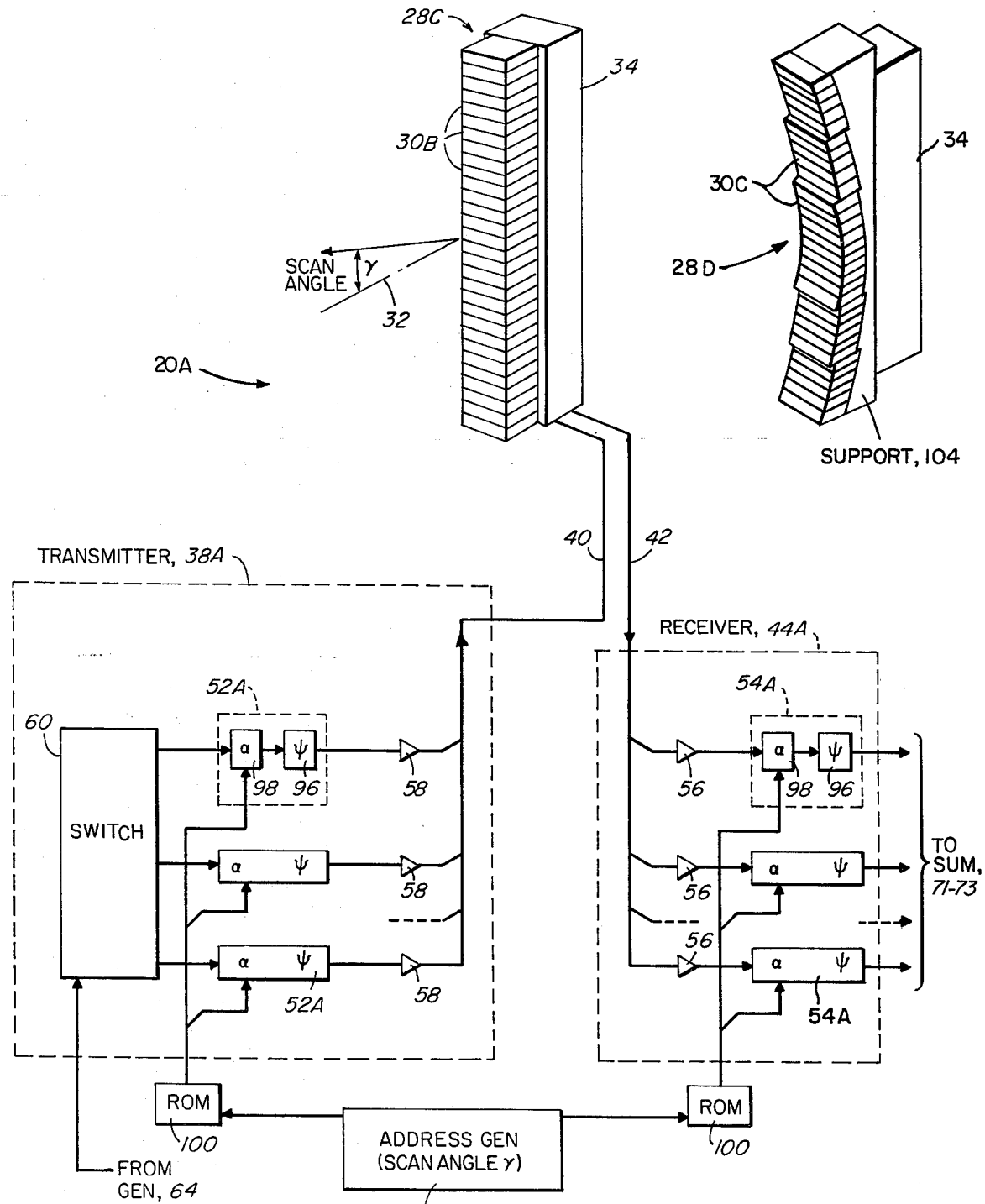

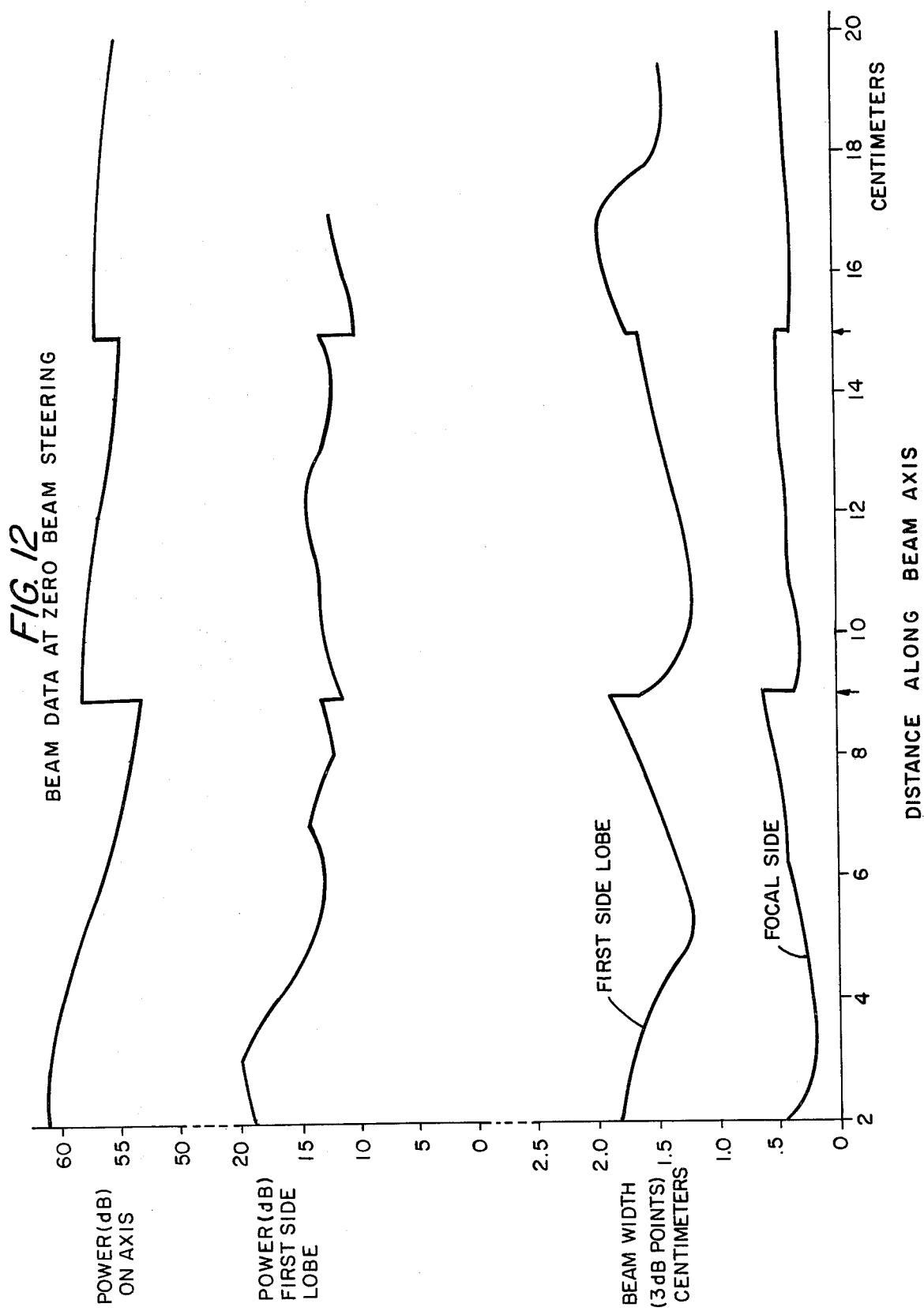

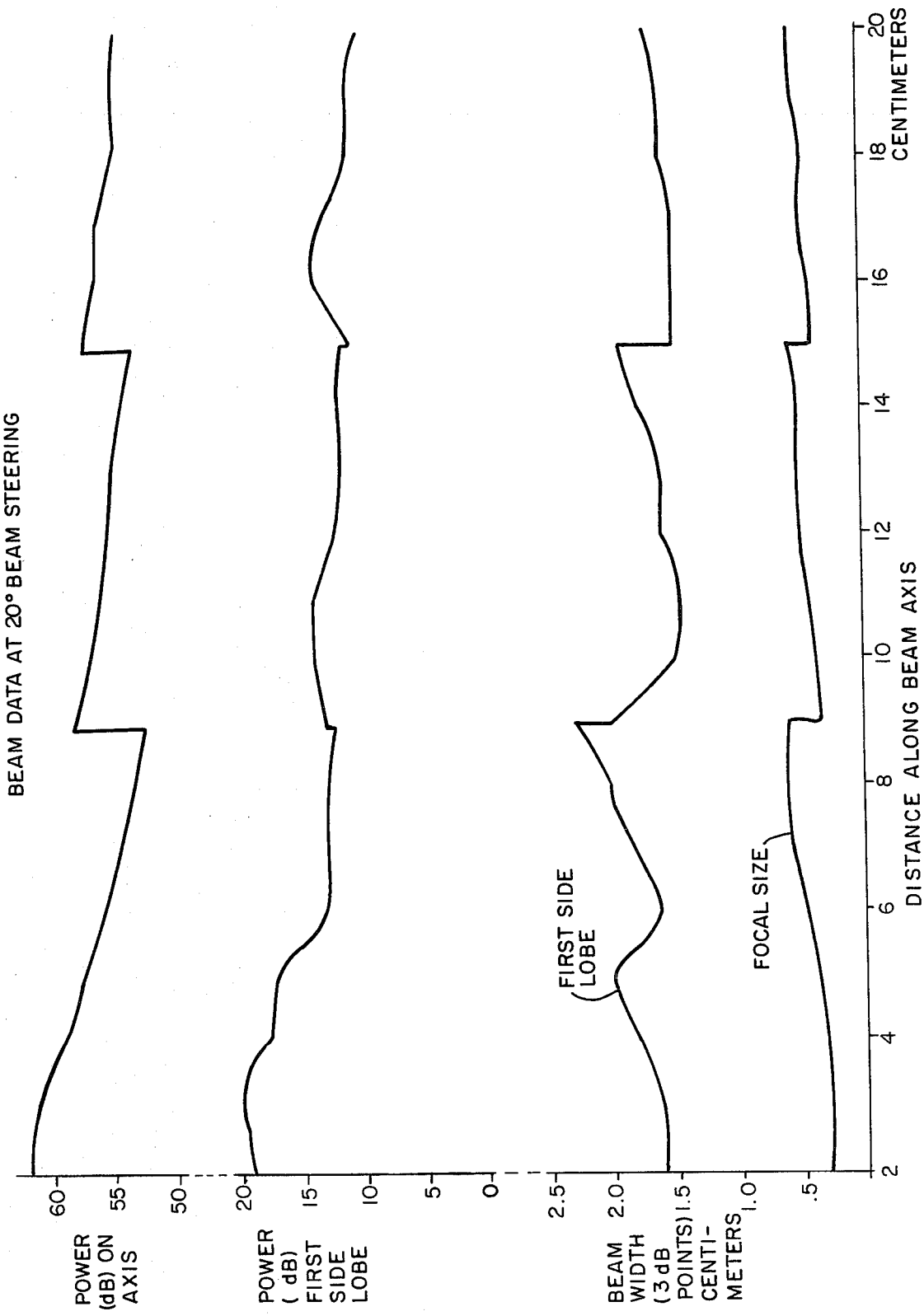

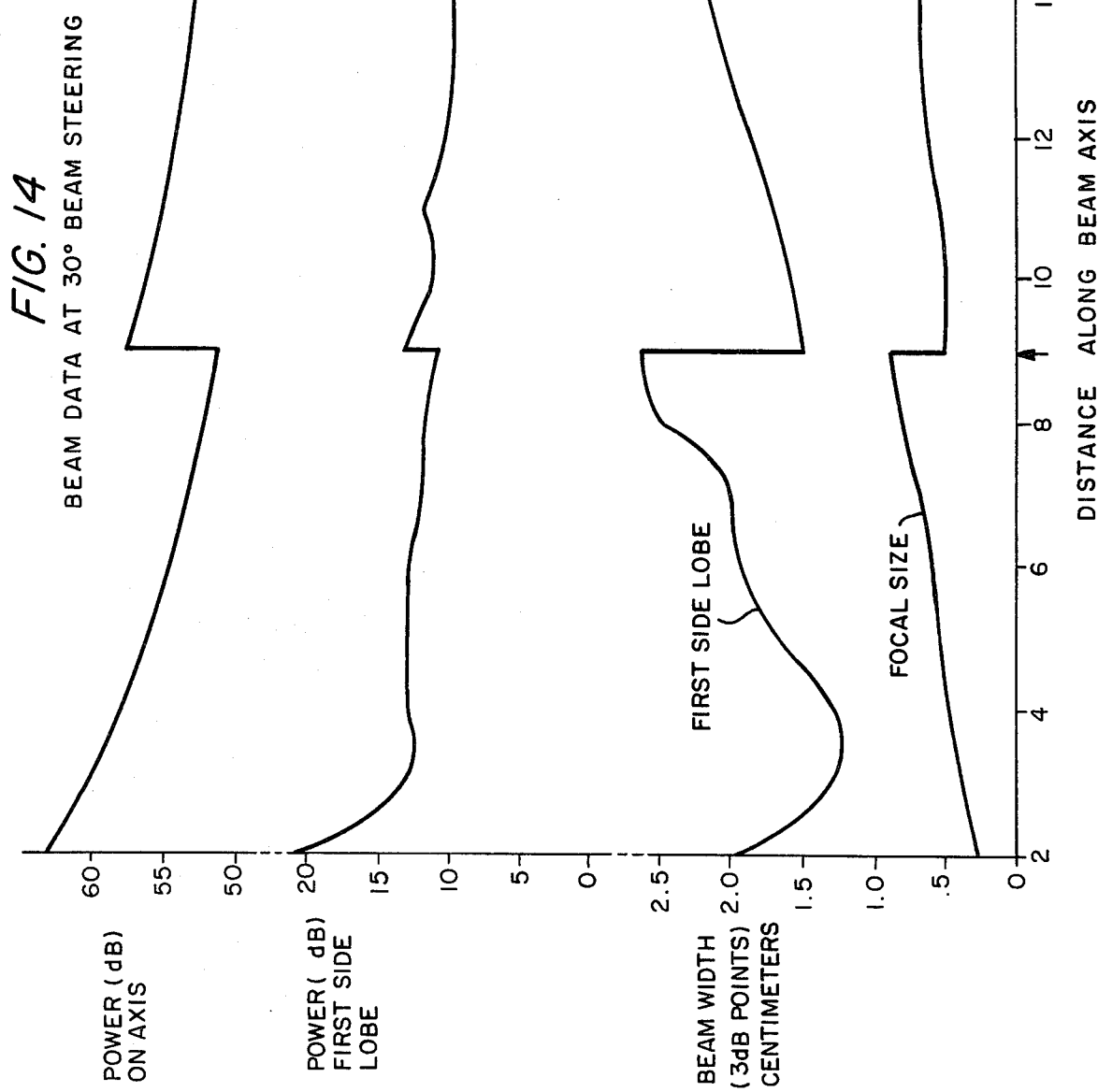

DYNAMICALLY FOCUSSED ARRAY

BACKGROUND OF THE INVENTION

Sonic imaging systems have been utilized for biological and medical situations were interior points of a subject are to be observed. Typically, such imaging systems employ a source of sound in the form of an array of a relatively large number of small transducers or, alternatively, in the form of one or more large transducers having a size commensurate with the overall size of the array. The source of sound may provide for parallel rays of radiation to focus at infinity, or may provide converging rays to focus at a nearby point.

By way of example, the U.S. Pat. No. 3,967,234 which issued in the name of Jones on June 29, 1976, shows the use of arcuate transducers to provide converging beams of radiation for focusing at a nearby point to produce better resolution in the near field. A similar source of sound, but being composed of an array of ultrasonic transducers having a preset curvature for focusing the radiant energy, is shown in the U.S. Pat. No. 3,587,561 which issued in the name of Ziedonis on June 28, 1971.

A problem exists in the use of the foregoing systems for imaging a biological or medical subject in that, generally, the systems are only focused at one predetermined range from the source of sound. Attempts at variable focusing by use of a transducer array with a tapped delay line for each transducer have resulted in excessive complexity and cost for a commercially acceptable system. By way of example in a medical imaging system, such as the imaging of the internal portion of a living creature, it may be desirable to accurately discriminate between bone material at one depth and flesh material at a second depth. However, the use of the foregoing fixed-focus sound sources requires the selection of a predetermined depth which will be focused, while points of interest at other depths will not be as well resolved.

SUMMARY OF THE INVENTION

The aforementioned problems are overcome and other advantages are provided by a system which focuses radiant energy at a plurality of foci. In accordance with the invention, the system incorporates an array of radiating elements wherein individual regions of the array form converging beams of radiant energy which focus, respectively, at individual foci spaced apart along a common axis of the beams. The principles of the invention apply both to electromagnetic energy and to sonic energy since both forms of energy are produced by radiating elements which may be placed in an array. The ratio of a diameter of a radiating aperture of the array to a wavelength of the radiant energy is chosen to provide for a moderately sharp focusing of the respective regions of the array so that the depth of field at one focus blends with the depth of field at the next focus. For example, in a preferred embodiment of the invention, a radiating aperture is provided which has a diameter equal to forty wavelengths, and which produces three foci with a spacing between the foci of eighty wavelengths. In the case of an array having circular symmetry about the beam axis, radiant energy of substantially uniform intensity is found within an elongated cylindrical region in front of the array and enclosing the foci.

In the case of medical ultrasonic imaging, the regions of the array may be separately activted upon transmission and reception of sonic energy directed toward a subject which is to be imaged. One or more of the regions of the array are activated for illuminating a specific region within the subject to be imaged. Upon reception of the echoes reflected from the subject, individual regions, or groups of the regions, of the array, are sequentially activated in synchronism with the time of propagation of the radiant energy through the subject to provide for a dynamic focusing of the array. The dynamic focusing permits the array to be focused at the points within the subject from which echoes of the radiant energy emanate.

The array may have a flat face or a curved face. In the case of the flat face, the array is composed of a set of radiating elements with focusing being accomplished by means of phase shifters or delay units coupled to each of the radiating elements to impart a phase shift or delay to electrical signals coupled to the radiating elements. The phase shift or delay is selected to produce a curved wavefront of radiation having a radius of curvature centered at the desired focus. In the case of the curved face, the array is focused by placing the radiating elements along a set of concave surfaces of constant radii of curvature, with the respective centers of curvature being at the desired foci. A separate curvature is applied for each of the foci. For the transmission of sonic energy from a planar array, the radiating elements take the form of relatively small sonar transducers fabricated of a piezoelectric material. Alternatively, in the case of a curved array transmitting sonic energy, a single large arcuate transducer may be utilized in lieu of a set of relatively small transducer elements positioned about the curved face of the array. The array of radiating elements takes the form of concentric circular regions wherein the innermost region is focused at the nearest focus while the outermost region is focused at the furthest focus.

In the case wherein the system provides an image of sites within a subject such as a human being, the array is advantageously placed against the subject, as in medical diagnostic imaging of a human being by sonic energy. Individual regions of the array are selected by a switch in rapid sequence to vary the focus as a function of the range of sites from which echoes emanate. To facilitate the description of the invention, the following description will relate to a sonic imaging system, it being understood that the description applies in an analogous fashion to a system utilizing electromagnetic radiation, such as a laser radar which may be focused at nearby points.

In one embodiment of the invention, three groups of sonic transducer elements are arranged in a planar array of concentric circular regions wherein the middle and the outer regions are of annular shape. Phase shifters providing fixed values of phase shift are employed for shifting the phases of signals of transducers in each of the circular regions. Thereby, for each circular region there is provided a wavefront which converges toward a fixed focal point upon transmission, and diverges from the fixed focal point toward the array upon reception. Delay lines having preset values of delay are preferred in lieu of the phase shifters for wide band signals since the delay lines have a wider bandwidth than the phase shifters. A different focal point is formed by each of the three regions.

For forming each of the focal points during reception of an echo, the transducer signals from each of the regions are separately combined to produce a sum signal for each region. The sum signal corresponds to an echo emanating from the vicinity of the site of the focus of the respective region. Circuitry, including a selector switch, sequentially selects a sum signal or a combination of sum signals as a function of the time of travel of an echo in the subject to provide effectively a dynamic focusing of the imaging system, the focus changing with the depth of the reflecting sites within the subject from which the echoes emanate. Thereby, enhanced resolution of individual points within the subject is provided to produce a sharper image of these points on a display.

In an alternative embodiment of the invention utilizing an array with three regions arranged on separate spherical surfaces, the outer and the middle regions of the array employ coaxial annular transducers disposed on spherical surfaces, while the central region employs a circular transducer having a spherical surface. Each of these three transducers has a concave cross-section to provide for the focusing of the sonic energy, the three transducers providing a set of three focal points. The selection of a focal range is accomplished by the selective switching of the three regions as has been described above for the first embodiment.

BRIEF DESCRIPTION OF THE DRAWINGS

The aforementioned aspects and other features of the invention are explained in the following description taken in connection with the accompanying drawings wherein:

FIG. 4 shows a sectional view, taken along the central axis, of an array of coaxial annular transducers in an alternative embodiment of the array of FIG. 1 wherein the planar surface of the array has been replaced with a set of concave surfaces, individual concave surfaces being used respectively for each of the circular regions, the curvature being shown exaggerated to facilitate illustration of the invention;

FIG. 7 is a block diagram of an alternative embodiment of the system of FIG. 1 employing a line array with beam scanning;

FIG. 8 is an isometric view of an alternative form of the line array of FIG. 7 wherein the transducers are arranged in arcs for focusing radiant energy;

FIGS. 12–14 show graphs of radiation intensity provided by arrays of the invention.

DESCRIPTION OF THE PREFERRED EMBODIMENT

Figure 1:
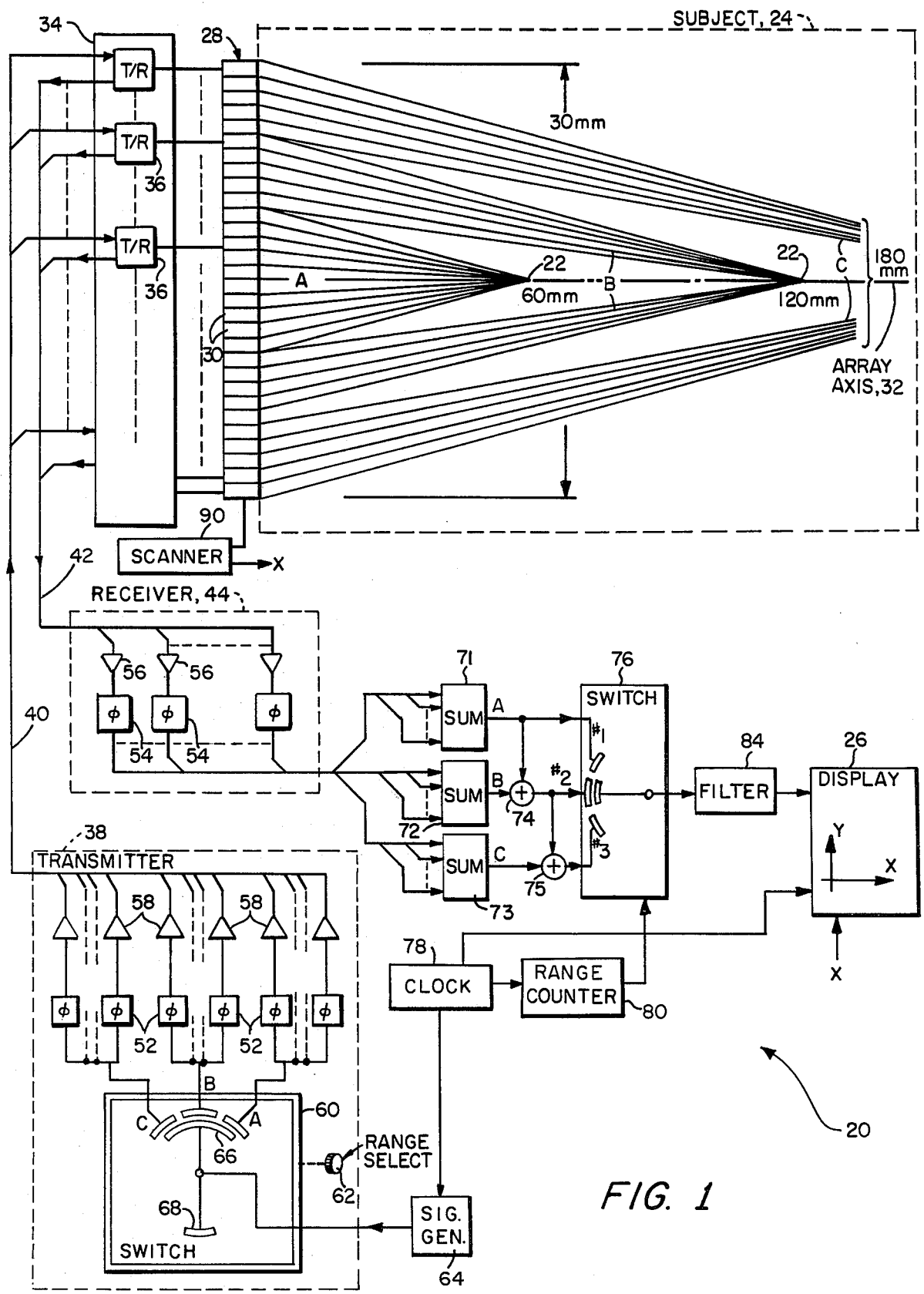
FIG. 1 is a block diagram of a system for forming an image of a subject, as in medical diagnostic imaging, the imaging system incorporating an array of transducers in accordance with the invention, the diagram showing a sectional view taken along the central axis of an array of coaxial annular sonic transducers positioned in a plane, the transducers being grouped in circular regions about a central region with each region focusing radiant energy toward a different focal point.
Figure 2:
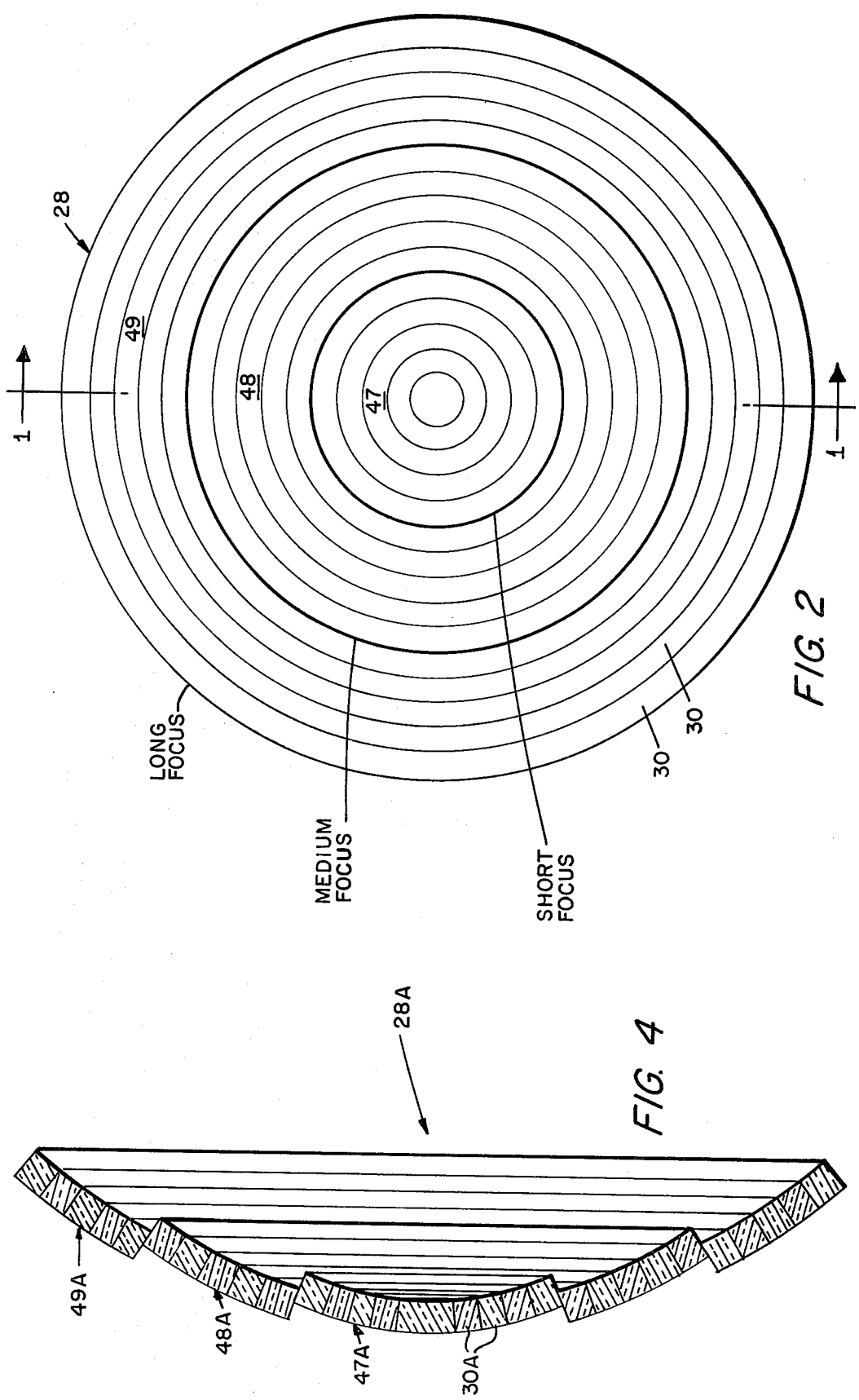
FIG. 2 is a front view of the array of FIG. 1, as seen looking along the axis of the array, the lines 1—1 therein designating the sectional view of FIG. 1.

Referring now to FIGS. 1 and 2, there is seen a system 20 for producing images of points 22 within a subject 24, the images being portrayed upon a display 26 of the system 20. The system 20 comprises a planar array 28 of annular sonic transducers 30 arranged in individual regions about a common axis 32 of the array 28. The transducers 30 may be fabricated of a piezoelectric material, such as lead-zirconate-titanate, with electrodes (not shown) attached to the material in a conventional manner. The system 20 further comprises a module 34 of transmit/receive circuits 36 which are coupled to respective ones of the transducers 30. Upon transmission, a set of signals is applied by the transmitter 38 via a line 40 and the module 34 to the transducers 30. The signals coupled via the line 40 are seen to fan out to individual ones of the circuits 36. Echo signals reflected from sites within the subject 24 and incident upon the transducers 30 are coupled via the circuits 36 and line 42 to a receiver 44.

In accordance with the invention, the array 28 comprises a central circular region 47 having a short focal length, an inner annular region 48 having a medium focal length, and an outer annular region 49 having a long focal length. Signals radiated by individual ones of the transducers 30 in the respective regions 47–49 are provided with phase shifts by corresponding phase shifters 52 in the transmitter 38, while signals received from the transducers 30 are provided with phase shifts by corresponding phase shifters 54 in the receiver 44. Each of the phase shifters 52 and 54 provides a single fixed value of phase shift. The receiver 44 comprises amplifiers 56 which are coupled to the input terminals of the respective phase shifters 54 whereby signals seen fanning into the amplifiers 56 from the line 42 are amplified to a sufficient magnitude for operation of the phase shifters 54. The transmitter 38 includes a set of amplifiers 58 for amplifying the power of signals provided by the phase shifters 52 to a sufficient magnitude for transmission into the subject 24. Also included in the transmitter 38 is a selector switch 60 operated by a knob 62 for selectively coupling a signal, produced by a signal generator 64, to the transducers 30 of one or more of the regions 47–49.

The rays of radiation from the central region 47 are identified in FIG. 1 by the legend A, the rays from the regions 48 and 49 being identified respectively by the legends B and C. While the rays from each of the regions 47–49 are focused at their respective focal points 22, it has been found advantageous, as will be explained hereinafter, to utilize the rays from a plurality of the regions 47–49 for the imaging of sites within the subject 24 at specific ranges from the array 28. As shown in FIG. 1, and by way of example, the rays A focus at a point 22 located at a distance of 60 mm (millimeters), the rays B focus at the point 22 located at a distance of 120 mm, and the rays C focus at a point located at a distance 180 mm from the array 28. All the focal points are on the axis 32. For receiving echoes from subject matter located at a distance in the range of 30 mm to 90 mm, only the transducers 30 of the central region 47, producing the rays A, are excited. For subject matter located at a distance in the range of 90 to 150 mm, the transducers 30 in both the regions 47–48, providing the rays A and B, are excited. For subject matter located at distances greater than 150 mm, the transducers 30 of all three regions 47–49 providing the rays A, B and C are excited.

The switch 60 is provided with three fixed contacts, labeled A, B and C, for coupling the signal from the generator 64 to the transducers 30 of the corresponding regions of the array 28. A sliding contact 66 of the switch 60 rotates past the fixed contacts and is sufficiently long for contacting all three contacts A, B and C simultaneously as shown in FIG. 1, the sliding contact 66 contacting only the contacts A and B, or simply the contact A upon rotation of the sliding contact. The sliding contact 66 is rotated by the knob 62 for selectively energizing the regions 47–49 of the array 28 in accordance with the range of distances of the subject matter to be imaged such that the rays A are radiated for short distances, the rays A+B are radiated for medium distances, and the rays A+B+C are radiated for long distances. The switch 60 may also be provided with a smaller contact 68 for individually selecting either the rays A, B, or C.

The system 20 also comprises summers 71–75, a switch 76, a clock 78, a range counter 80 and a filter 84. The clock 78 provides timing signals for synchronizing the operation of the display 26 with the operation of the counter 80 and the signal generator 64. The switch 76 is portrayed as a mechanical switch to facilitate the explanation of its operation; however, it is understood that the switch 76 operates electronically in response to a digital signal of the counter 80 representing the range of subject matter from which echoes emanate in the subject 24. A sliding contact of the switch 76 selectively couples signals from one of three terminals #1, #2 and #3.

The summer 71 sums together the transducer signals of the central region 47, corresponding to the rays A, and applies the sum to terminal #1 of the switch 76. The summer 72 sums together the transducer signals of the inner annular region 48, corresponding to the rays B, and applies the sum to the summer 74. The summer 74 combines the output signals of the summers 71–72 and applies the combined signal, corresponding to the rays A+B to terminal #2 of the switch 76. Similarly, the summer 73 sums together the transducer signals of the outer annular region 49 and applies the sum to the summer 75, the summer 75 combining the sums of the summers 73–74 and applying the combined signal, corresponding to the rays A+B+C to the terminal #3 of the switch 76. Thereby, in response to a range signal from the counter 80, the switch 76 applies the corresponding set of transducer signals to the filter 84 for presentation of the display 26. The filter 84, as well as the phase shifters 52 and 54, have a sufficiently wide pass band to accommodate the transducer signals. The filter 84, preferably, is matched to the waveform of the signal provided by the generator 64 to maximize the power of received echo signals relative to background noise.

In the preferred embodiment of the invention, the array 28 has an exemplary diameter of 30 mm. The wavelength of sonic energy produced by the array 28 has an exemplary value of ¾ mm in water (or human tissue) at an exemplary frequency of 2 MHz. The transducers 30 each have a radiating aperture with an exemplary dimension in their radial direction of ½ mm, this being equal to ⅔ wavelength.

In operation, the phase shifters 52 coupling signals to the transducers 30 of the central region 47 are each preset with individual values of phase shift to produce a curved wavefront for radiation emanating from the central region 47, the wavefront being curved about the near focal point 22. Similarly, the phase shifters 52 coupling signals to the transducers 30 of the inner annular region 48 and the outer annular region 49 are each provided with individual values of phase shift for providing curved surfaces of wavefronts emanating from the respective regions 48–49, the wavefronts being curved respectively about the middle focal point 22 and the far focal point 22, respectively. Thereby, the phase shifters 52 provide for the focusing of the signals from the array 28. Similar comments apply to the operation of the phase shifters 54 for providing a focusing upon reception of the echoes from the subject 24. In response to a timing signal of the clock 78, the signal generator 64 provides the waveform of the signal to be transmitted by the transducers 30. The clock 78 further provides timing pulses to the counter 80, which counts these pulses to provide the time elapsed from the transmission of the signal of the generator 64.

A feature of the invention is the dynamic focusing which can readily be accomplished since the three regions of FIG. 1 are preset to focus at their respective focal lengths. The time elapsed between the transmitted signal and the reception of an echo from a site within the subject 24 is a measure of the distance, or range, of the site from the array 28. The counter 80 drives the switch 76 to couple echoes from different focal regions as a function of range. Thus, at short ranges, the display 26 is presented with signals received via the central region 47 of the array 28, while for moderate ranges the display 26 is presented with signals received by the combination of both the central region 47 and the inner annular region 48. At large ranges, the display 26 is presented with signals received by the combination of the three regions 47–49 of the array 28. The use of all three regions 47–49 at the longer ranges, while only the region 47 is used at close range, provides greater uniformity of sound intensity at the various ranges without significant degradation of focal spot size.

The knob 62 of the switch 60 is utilized to select the optimum mode of transmission. Thus, by way of example, if all regions within the subject 24 are of equal interest, then the switch 60 is set as shown in the figure such that all transducers 30 of the array 28 are transmitting. However, if subject matter at moderate or nearby ranges is primarily of interest, then the switch 60 is set for coupling the signals, respectively, via the contacts A and B or only via the contact A. If desired, the sliding contact 68 may be utilized for coupling signals by the contact B or the contact C.

Figure 3:
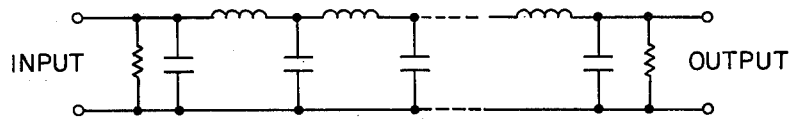
FIG. 3 is a schematic diagram of a delay line for delaying transducer signals in an alternative embodiment of the system of FIG. 1.

Referring also to FIG. 3, there is seen a schematic diagram of a delay line which may be utilized in lieu of a phase shifter 52 or 54 in an alternative embodiment of the invention wherein the focusing of the radiant energy is to be accomplished by a delaying of the transducer signals rather than by providing the phase shift as has been described with reference to FIG. 1. The delay line takes the form of an inductor-capacitor ladder circuit with terminating resistors at the input and output terminals thereof. Such a delay line has an exemplary bandwidth of approximately 10 MHz (megahertz) which is well in excess of the frequency of the radiant energy, such frequency being typically on the order of 1–2 MHz which is used in sonic imaging for medical diagnostic purposes. Thereby, a burst of the radiant energy having a duration of approximately one cycle of the radiant energy can be accommodated by the system of FIG. 1, the corresponding electrical signal being readily propagated through the delay line of FIG. 3 without significant distortion.

Referring also to FIG. 4, there is shown a cross-sectional view of an alternative embodiment of the array 28 of FIGS. 1 and 2, the alternative embodiment of FIG. 4 being identified by the legend 28A. Annular sonic transducers 30A of FIG. 4 are arranged in three regions 47A, 48A and 49A which correspond respectively to the central region 47, the inner annular region 48 and the outer annular region 49 of FIG. 2. The embodiment of FIG. 4 differs from that of FIGS. 1 and 2 in that the front faces of each of the regions 47A–49A are concave with radii of curvature directed respectively from each of the three focal points 22 of FIG. 1, this being in contradistinction to the planar surfaces of the regions 47–49 of FIGS. 1 and 2. The radius of curvature of the central region 47A of FIG. 4 is directed from the nearest of the points 22 while the radii of curvature of the regions 48A and 49A are directed respectively from the points 22 at 120 mm and 180 mm in FIG. 1.

The concavity of each of the regions of the array 28A provides a curved wavefront of radiation and a focusing of the radiation from each of the regions to the respective focal points 22 on the array axis 32. Since the curvature of the wavefronts provided by the array 28A is the same as that provided by the planar array 28 of FIG. 1 in conjunction with the phase shifters 52 and 54, the phase shifters 52 and 54 may be deleted, or be set for equal values of phase shift, when the array 28A is utilized. A further feature of the array 28A is the displacing, or stepping, of the respective regions 47A–49A relative to each other along the array axis. The stepping results in a shifting of the nominal phase of the groups of rays A, B and C relative to each other to provide for a constructive addition of the respective radiation at numerous points along the axis 32 of FIG. 1. The stepping may be accomplished physically by the physical locations of the regions 47A–49A as shown in FIG. 4, or electrically by the use of delay lines, such as that of FIG. 3, in which a fixed delay is imparted to sigals of one region relative to another of the regions 47A–49A. An adjustment in the location of the regions 47A–49A will be described with reference to FIG. 10. The constructive addition results in uniformity of energy density along the axis 32 will be seen in the graphs of FIGS. 12–14. Alternatively, the set of phase shifters 52 and the set of phase shifters 54 may be used to impart a phase taper to the transducers 30A in one or more of the regions 47A–49A to alter the positions of the corresponding focal points 22 along the axis 32. If desired, switches (not shown) may be employed for bypassing the phase shifters 52 and 54 whereby the phase taper may be selectively introduced to establish additional ones of the focal points 22 for the dynamic focusing.

Figure 5:
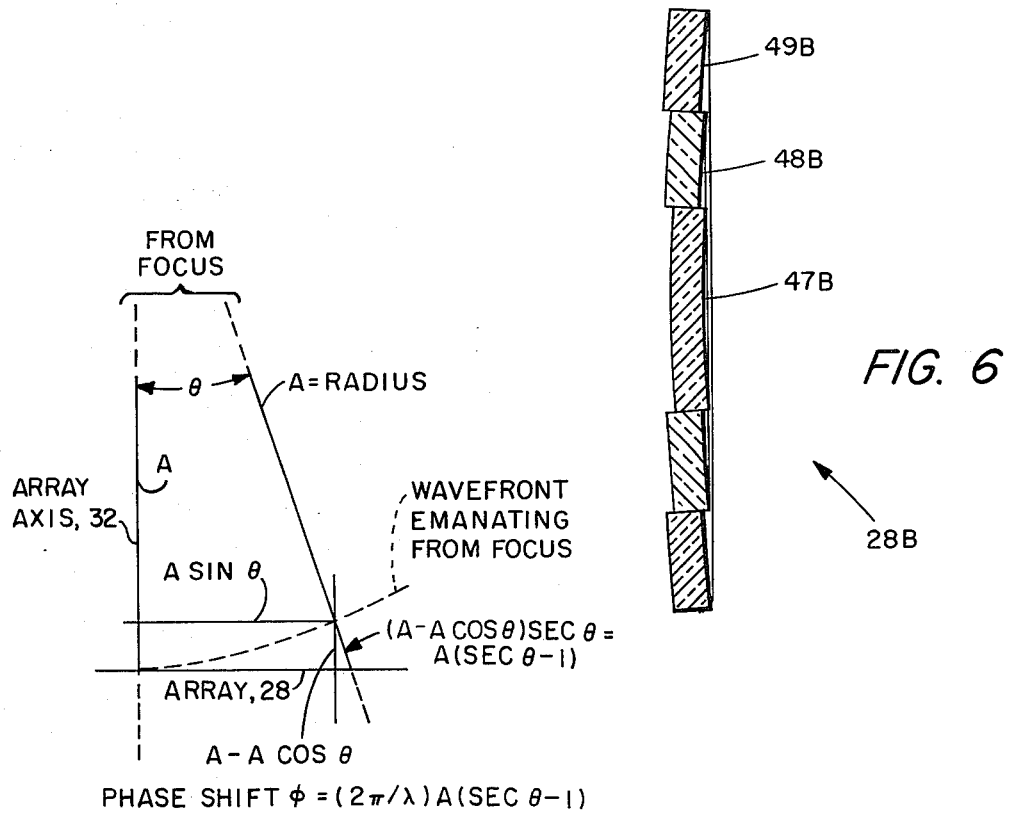
FIG. 5 shows a geometric construction useful in calculating the phase shifts required for focusing the radiant energy of the transducers in each region of FIG. 1 toward a specific focus.

Referring also to the diagram of FIG. 5, and with reference to the case of the planar face of the array 28 of FIGS. 1 and 2, the focusing at the respective focal points is accomplished, as has been noted hereinabove, by introducing phase shifts to signals transmitted by and incident upon the transducers 30 by the phase shifters 52 and 54. The magnitudes of the phase shifts as a function of position along the array 28 are shown by the diagram and are maintained constant during the transmission and reception of the sonic energy. For each transducer 30, the amount of the phase shift compensates for signal delay experienced in the transition from the concave regions 47A–49A of FIG. 4 to the planar faces of the corresponding regions of FIG. 2. Similarly, when delay lines, such as that of FIG. 3, are utilized in lieu of the phase shifters 52 and 54, calculation of the compensating delay follows the calculation of the phase shift shown in FIG. 5 for the exemplary wavelength of $\frac{3}{4}$ mm. For the exemplary dimension of array size and focal distances shown in FIG. 1, it is seen that the outer diameter of each of the regions of the arrays 28 and 28A bears a ratio of 1:6 relative to the corresponding focal distances. As seen by the trignometric construction of FIG. 5, the necessary phase compensation for the planar surface approaches a magnitude of approximately $\pi/3$ radians at the outer radius of any one of the regions 47–49 relative to locations at the inner radii of the corresponding regions. The foregoing explanation also applies to the alternative phase taper for the array 28A of FIG. 4 and to a line array which will be described in FIG. 7.

If desired, the array 28 may be translated in position along the surface of the subject 24 by conventional means, represented by a scanner 90, to provide a two dimensional presentation on the display 26, wherein the Y coordinate represents depth within the subject 24 while the X coordinate represents distance along the surface of the subject 24. The scanner 90 produces a signal at its X terminal which is coupled to the X terminal of the display 26 for driving the X axis of the display 26 in correspondence with the X position of the array 28. By way of alternative embodiments, it is also noted that the switch 76 may also be provided with a small moving contact (not shown) such as that described previously with to the switch 60, plus additional contacts coupled directly to the output terminals of the summers 72 and 73 whereby signals may be coupled individually from the regions B and C. Such a switching arrangement may prove useful in eliminating off-axis signals in the vicinity of a focal point 22. However, the switching arrangement actually shown in FIG. 1 is generally preferred because of the uniformity of intensity provided at intermediate points between the focal points 22 as will be described hereinafter.

Figure 6:
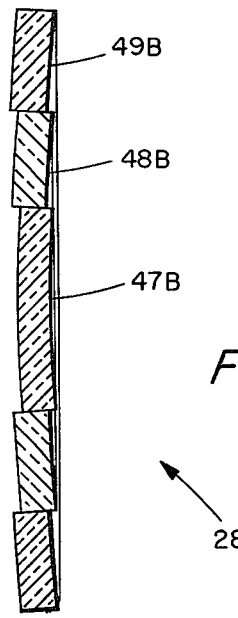
FIG. 6 shows a sectional view, taken along the central axis, of an array of coaxial annular transducers in a further embodiment of the array of FIG. 1, similar to that of FIG. 4, wherein the transducers in each region of FIG. 4 have been replaced wih a single, relatively large, transducer having a concave face.

Referring now to FIG. 6, there is seen a further embodiment of the array 28 of FIG. 1, the alternative embodiment of FIG. 6 being identified by the legend 28B. The array 28B is similar to the array 28A of FIG. 4 in that concave radiating surfaces are employed. However, in lieu of the numerous annular transducers having a relatively thin form for providing each of the three regions 47A–49A of FIG. 4, the embodiment of FIG. 6 employs a single annular transducer for each of the regions 48B and 49B, and a single bowl-shaped transducer for the region 47B. The radiating surface of each of the transducers has the curvature of a spherical surface. Focusing of radiant energy with the array 28B is accomplished in the same manner as taught previously with reference to the array 28A. However, great simplicity of the electronic circuitry is provided in that only three transducer elements are employed in the array 28B.

Referring now to FIG. 7, there is seen a system 20A which is an alternative embodiment of the system 20 of FIG. 1, the system 20A comprising a line array 28C of rectangular transducers 30B in lieu of the circular array 28 of annular transducers 30 in the system 20. The array 28C of FIG. 7 is coupled via the module 34 of transmit/receive circuits, and then via the line 40 to a transmitter 38A, and via the line 42 to a receiver 44A. The transmitter 38A comprises the switch 60 and the amplifiers 58 and is coupled to the generator 64 as is the case with the transmitter 38 of FIG. 1. Also, the receiver 44A comprises the amplifiers 56 which are coupled to the summers 71-73 as is the case with the receiver 44.

In accordance with a feature of the invention, both dynamic focusing (as was taught for the system 20 of FIG. 1) and beam steering are provided for the line array 28C of FIG. 7. The combination of dynamic focusing and beam steering is provided by phase shifting circuits 52A and 54A which incorporate both a fixed phase shifter 96 and a variable phase shifter 98. For steering a beam through a scan angle which is less than approximately 20 degrees from the nominal axis of the radiation pattern, the focusing can be accomplished by the use of the fixed phases, as is provided by the phase shifters 52 and 54 of FIG. 1, plus a variable phase shift which is tapered linearly from one end of the array 28C to the other end of the array 28C to tilt the wavefront for focusing at a point off the axis of the array. For a nominal axis of the radiation pattern which is inclined at a relatively large angle, greater than 20 degrees, the acuity of the focus is diminished and additional compensating electronic circuitry is needed.

The fixed values of phase shift are provided by the shifters 96, and the variable shifters 98 provide phase shifts according to digital control signals from read-only-memories 100 in response to an address from an address generator 102. The address generator 102 provides an address in accordance with the desired scan angle. The address may be designated manually by an encoder (not shown) in the generator 102, or the address may be provided by a counter (not shown) which is in the generator 102 and is responsive to timing signals from the clock 78 of FIG. 1. Each of the memories 100 stores a set of values of phase shift for the phase shifters 98, and produces the aforementioned control signals in accordance with the phase shift required to direct the axis of the radiation pattern in in the desired direction.

FIG. 8 shows an array 28D mounted on a support 104 through which transducers 30C of the array 28D are coupled to the module 34. The array 28D may also be referred to as a line array, and may be regarded as a slice of the array 28A of FIG. 4. The array 28D of FIG. 8 may be utilized in lieu of the array 28C in the system 20A of FIG. 7, in which case the fixed phase shifters 96 may be deleted since the focusing is accomplished by the curvatures of the regions of the array 28D in a manner analogous to that explained above with reference to the array 28A of FIG. 4.

Figure 9:
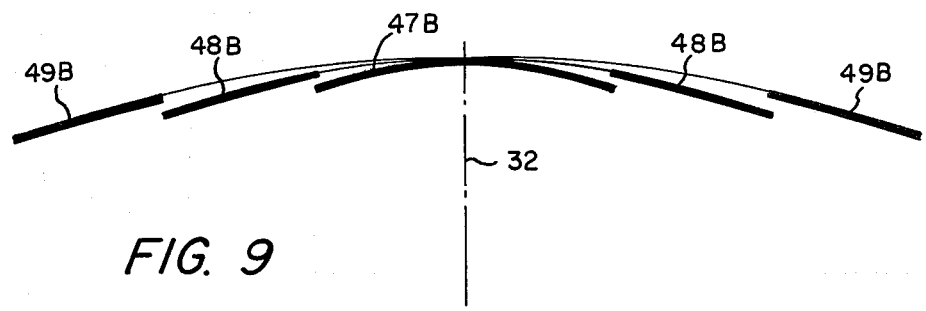
FIG. 9 shows a diagram of tangential curvature of a set of regions of the array of FIG. 8, the diagram also being applicable to a cross-section of the arrays of FIGS. 4 and 6.

Referring now to FIG. 9, there is seen a diagrammatic view of the concave radiating surfaces of the array 28D of FIG. 8, the diagrammatic view being equally applicable to a cross-section of the arrays 28A-B of FIGS. 4 and 6. The arcs representing the surfaces of the respective regions are shown exaggerated in order that the curvature be more visible. The arcs are shown extended to intersect the axis 32 and have been positioned so as to be tangent at a common point on the axis 32.

Figure 10:
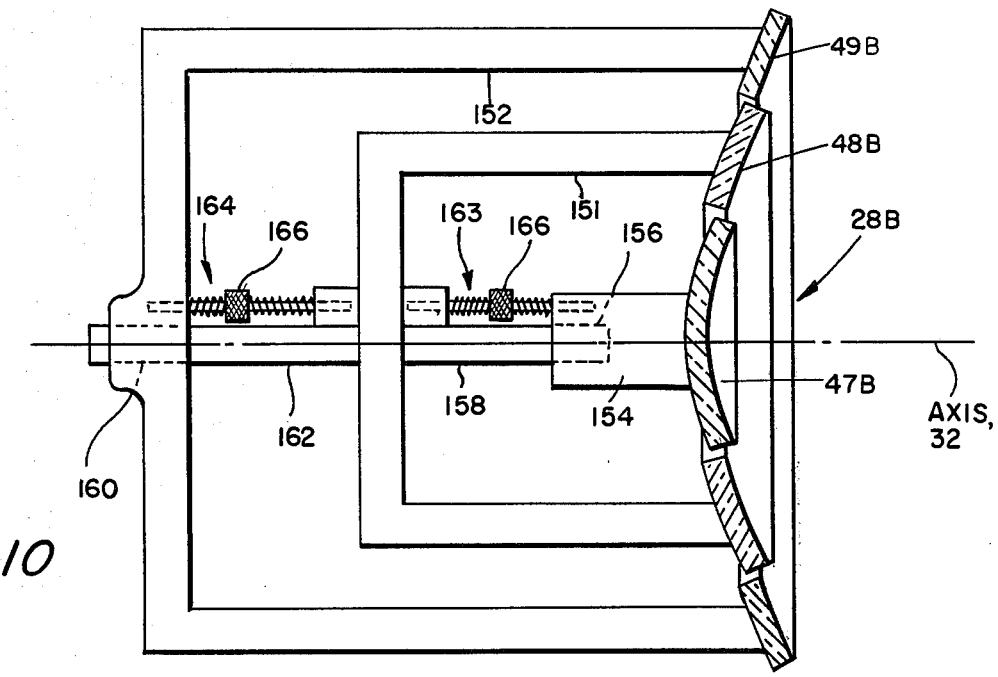
FIG. 10 shows a mechanical structure for positioning the regions of the arrays of FIGS. 4 and 6.

Referring also to FIG. 10, there is seen a mechanical arrangement for supporting the regions 47B-49B of the array 28B of FIG. 6. The mechanical supporting structure comprises yokes 151 and 152 which are affixed to the regions 48B-49B, respectively, of the array 28B. The region 47B is affixed to a pedestal 154 having a keyway 156 therein for sliding on a rail 158 which is rigidly secured to the center of the yoke 151. Similarly, the yoke 152 is provided with a keyway 160 for sliding on a rail 162 which is rigidly secured to the central portion of the yoke 151. Double threaded screws 163-164 having knobs 166 thereon are threaded between the central portion of the yoke 151 and, respectively, the pedestal 154 and the yoke 152 for urging the pedestal 154 and the yoke 152 into positions relative to the yoke 151. Thereby, the region 47B and the region 49B may be displaced along the axis of the array 28B relative to the region 48B to adjust the relative phases of the groups of rays A, B and C which were seen in FIG. 1. Following the construction of FIG. 9, the surfaces of the regions 47B-49B of FIG. 10 may be viewed as extending to the axis 32. The tangents to such extensions of the curved surfaces of the respective regions 47B-49B at the axis 32 are parallel to each other. By turning the knobs 166 for adjusting the screws 163-164, the respective tangents may be made to coincide as shown in the diagrammatic view of FIG. 9. Alternatively, the regions 47B-49B may be displaced relative to each other so as to eliminate the stepped appearance and providing a continuous surface for the entire array 28B.

Figure 11:
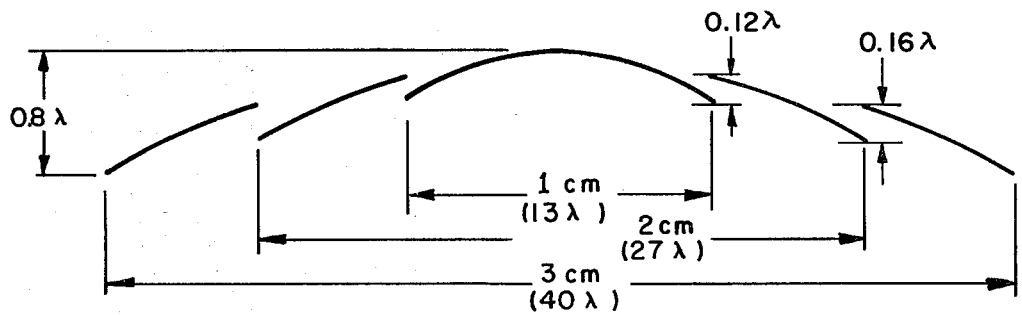
FIG. 11 shows a diagram of the curved regions of the array of FIG. 8 with the dimensions in terms of wavelengths.

Referring now to FIG. 11, there is seen a diagrammatic view similar to that of FIG. 9, FIG. 11 showing dimensions of the array 28D of FIG. 8 in terms of wavelengths, the diameters also being seen in centimeters. The displacements between the regions of the array are shown as 0.12 wavelengths in the axial direction between the central region and the inner annular region, and a distance of 0.16 wavelengths in the axial direction between the inner and outer annular regions. The aperture diameters are shown respectively as 13 wavelengths, 27 wavelengths and 40 wavelengths for the three regions of the array. The depth of the radiating surface of the array as measured along the axis is 0.8 wavelengths. For ease of mathematical analysis, it is more convenient to describe the curved line array 28D of FIG. 8 than the two dimensional bowl-shaped arrays of FIGS. 4 and 6. Accordingly, in the ensuing FIGS. 12-14, a curved line array having the dimensions outlined in FIG. 11 is to be utilized.

Referring now to FIGS. 12-14, there is presented a set of graphs showing patterns of the intensity of radiation at locations both on the axis and off the axis of a curved line array 28D of FIG. 8 having the dimensions shown in FIG. 11. These graphs closely approximate the radiation patterns for a bowl-shaped array such as that of FIGS. 4 and 6 wherein the dimensions in a longitudinal axial plane are those portrayed in FIG. 11. The focal points are located at distances of 60 mm, 120 mm and 180 mm in front of the array, these being the same locations as was described previously with reference to FIG. 1. In developing the graphs of the FIGS. 12-14, it is assumed that the central region producing the group of rays A is activated from 0 to 90 mm distance, that the central region and the inner annular region for the groups of rays A and B are activated for distances in the range of 90 to 150 mm, and that all three regions for providing the groups of rays A, B and C are energized over the range of distances 150 mm to 200 mm. It is seen that the radiation pattern can be brought to a focus of intermediate acuity over the aforementioned range of distances. In particular, it is noted that, with reference to the fourth graph of FIG. 12, the size of the focus is generally less than one-half centimeter throughout the range of 20 centimeters. If the array had only a single curved region, rather than the three regions outlined in FIG. 11, then the focal spot would have increased to 2 centimeters at some points within the 20 centimeter range. The first graph of FIG. 12 shows the power per unit area (or intensity) in decibels along the axis of the array while the second graph shows the intensity in decibels of the first sidelobe of the radiation pattern. The third graph shows the beam width as measured at the first sidelobe of the radiation pattern while the fourth graph, as already noted, gives the width of the focal spot.

In the description of the array of FIG. 7, it was shown that the axis of the radiation pattern can be scanned relative to the axis of the array. Accordingly, in FIG. 13 there is presented a set of graphs which correspond to the four graphs of FIG. 12, the graphs of FIG. 13 providing the intensity on the axis of the beam, the intensity on the first sidelobe, the width at the first sidelobe and the width of the focal size for a radiation pattern which has been steered 20° off of the array axis. FIG. 14 portarys the foregoing four relationships for the case of a radiation pattern, or beam, which has been steered at an angle of 30° relative to the array axis. The focus retains its acuity and substantial uniformity of size for beam steering angles less than 25°.

As was noted hereinabove, the graphs of the FIGS. 12–14 were developed for the situation wherein the tangents to the curves of FIGS. 9 and 11 coincide at the axis 32. However, by altering the positions of the arcs, as by the mechanism described in FIG. 10, the size of the focus can be optimized.

It is understood that the above-described embodiments of the invention are illustrative only and that modifications thereof may occur to those skilled in the art. Accordingly, it is desired that this invention is not to be limited to the embodiments disclosed herein but is to be limited only as defined by the appended claims.

What is claimed is:

1. A dynamically focused radiant energy system comprising:
    an array of fixed- focused radiators of radiation, each of said radiators having a different radius of curvature to provide a focus along an axis different from the others of said radiators;
    a receiver for receiving signals of said radiators;
    means for coupling said receiver to said array; and wherein
    said coupling means includes means synchronized to the propagation of a signal of said radiation for coupling one or more successive said radiators to said receiver, said successive radiators being coupled to said receiver in the order of their increasing focal distance to cause the focal point to move in the same direction and in correspondence with the propagation distance of said synchronized radiation.

2. A system according to claim 1 wherein each of said radiators is segmented and comprises a set of radiating elements each having their respective radiating apertures arranged along a curve having said fixed radius for focusing at the focus of the radiator formed by each set of elements.

3. A system according to claim 1 wherein said radiant energy is sonic energy, and wherein at least one of said radiators has an annular shape with a concave radiating surface of said radius for directing sonic energy toward a focus.

4. The array of claim 1 comprising in addition:
    the ratio of the diameter of each said radiator to a wavelength of the radiant energy providing a depth of focus of each said radiator which has a depth of field of focus which blends with the depth of field at the focus of the adjacent aperture.

5. A dynamically focused radiant energy system comprising:
    an array of fixed-focused radiators of radiation, each of said radiators having a focus different from any other of said radiators;
    a transmitter for transmitting a signal via said radiators;
    a receiver for receiving a signal via said radiators; and
    means for selectively coupling said transmitter and said receiver to said radiators of the array; said coupling means being synchronized to the transmission of said signal by said transmitter for sequentially coupling said radiators of greater focal length to said receiver.

6. A system according to claim 5 wherein said sequential coupling of radiators is accomplished at a rate equal to the rate of propagation of said radiation from a focus of one of said radiators to a focus of the next longer focal length of said radiators.

7. An array of radiating elements comprising:
    a plurality of arcuate radiators, arcs of constant radius defining the radiating surfaces of said radiators each one being of a different radius and being coaxial about an axis of said array the radius of each arc being constant with respect to a different focal point on said axis; and
    means for mechanically displacing said radiators longitudinally relative to each other along said axis.

* * * * *

UNITED STATES PATENT OFFICE
CERTIFICATE OF CORRECTION

Patent No. 4,276,779                Dated July 7, 1981

Inventor(s) Luther Davis, Jr.

It is certified that error appears in the above-identified patent and that said Letters Patent are hereby corrected as shown below:

Column 1, line 2, delete --were-- and replace with --where--;

Column 2, line 2, delete --activted-- and replace with --activated--;

Column 7, line 54, delete --sigals-- and replace with --signals--;

Column 11, line 33, delete --portarys-- and replace with --portrays--.

Signed and Sealed this

Twentieth Day of April 1982

|SEAL|

Attest:

Attesting Officer

GERALD J. MOSSINGHOFF

Commissioner of Patents and Trademarks